(12) United States Patent
Tian et al.

(10) Patent No.: US 11,776,174 B1
(45) Date of Patent: Oct. 3, 2023

(54) FLUORESCENCE MOLECULARTOMOGRAPHY RECONSTRUCTION METHOD BASED ON PRIOR GUIDANCE OF MAGNETIC PARTICLE IMAGING

(71) Applicant: BEIHANG UNIVERSITY, Beijing (CN)

(72) Inventors: Jie Tian, Beijing (CN); Yu An, Beijing (CN); Guanghui Li, Beijing (CN); Yang Du, Beijing (CN); Daxiang Yan, Beijing (CN); Jiaqian Li, Neijing (CN)

(73) Assignee: Beihang University

( * ) Notice: Subject to any disclaimer, the term of this patent is extended or adjusted under 35 U.S.C. 154(b) by 0 days.

(21) Appl. No.: 18/111,879

(22) Filed: Feb. 20, 2023

(51) Int. Cl.
| | |
|---|---|
| *G06T 11/00* | (2006.01) |
| *G06T 7/33* | (2017.01) |
| *G06T 7/73* | (2017.01) |
| *G06T 7/50* | (2017.01) |
| *G06T 9/00* | (2006.01) |
| *G06T 7/00* | (2017.01) |
| *A61B 5/00* | (2006.01) |
| *A61B 5/0515* | (2021.01) |
| *G06T 7/136* | (2017.01) |

(52) U.S. Cl.
CPC .......... *G06T 11/008* (2013.01); *A61B 5/0071* (2013.01); *A61B 5/0073* (2013.01); *A61B 5/0515* (2013.01); *G06T 7/0012* (2013.01); *G06T 7/136* (2017.01); *G06T 7/33* (2017.01); *G06T 7/50* (2017.01); *G06T 7/73* (2017.01); *G06T 9/00* (2013.01); *G06T 11/005* (2013.01); *G06T 2200/04* (2013.01); *G06T 2207/10064* (2013.01); *G06T 2207/10081* (2013.01); *G06T 2207/10101* (2013.01); *G06T 2207/30096* (2013.01); *G06T 2211/424* (2013.01)

(58) Field of Classification Search
CPC ......... G06T 11/008; G06T 7/136; G06T 7/50; G06T 7/73; G06T 7/33; G06T 7/0012; G06T 9/00; G06T 11/005; G06T 2200/04; G06T 2207/10064; G06T 2207/10081; G06T 2207/10101; G06T 2207/30096; G06T 2211/424; A61B 5/0071; A61B 5/0073; A61B 5/0515
See application file for complete search history.

(56) References Cited

PUBLICATIONS

Dong et al. "A fast reconstruction algorithm for fluorescence molecular tomography with sparsity regularization". (Year: 2010).*

* cited by examiner

*Primary Examiner* — Vu Le
*Assistant Examiner* — Winta Gebreslassie

(57) ABSTRACT

A fluorescence molecular tomography reconstruction method includes: obtaining an MPI three-dimensional tomographic image, a body surface near-infrared fluorescence two-dimensional image, and a CT image; constructing an SIS capable of accommodating the ROI, and discretizing the SIS by using a finite element method; performing data mapping to obtain detected surface fluorescence signals, a prior of the anatomical structure of tissues and organs around the tumor and a prior of the tumor; performing forward model calculation to obtain a system matrix and constructing an objective function; iteratively solving the objective function based on the Laplacian regularization matrix to obtain a fluorescence molecular tomography reconstruction result; the present invention adopts MPI to guide the FMT, achieving complete morphology and structure, clear tissue edges, and high accuracy of spatial position.

6 Claims, 4 Drawing Sheets

(Abstract)

Mouse in test     MPI image     Near-infrared fluorescence image     CT image

◻ Mark point 1     ○ Mark point 2     △ Mark point 3

FLUORESCENCE MOLECULARTOMOGRAPHY RECONSTRUCTION METHOD BASED ON PRIOR GUIDANCE OF MAGNETIC PARTICLE IMAGING

TECHNICAL FIELD

This invention generally relates to the field of fluorescence molecular tomography, and more particularly, to a fluorescence molecular tomography reconstruction method based on prior guidance of magnetic particle imaging.

BACKGROUND

Fluorescence molecular tomography (FMT) is capable of compensating for the weakness that two-dimensional fluorescence molecular imaging (FMI) fails to provide three-dimensional spatial information. Based on the fluorescence signal detected on the surface of a living body and the photon propagation model in the living body, the specific fluorescence distribution of the probe in the living body can be obtained by reverse acquisition, and the position and structure of a tumor can be further reconstructed. However, due to the nonlinear relationship between the measured flux on the surface and the fluorescence source (i.e., a tumor) in spatial position and signal intensity, and the complex and severe scattering and absorption effects of photon transmission in tissues, the fluorescence photons capable of reaching the surface of the fluorescence source at the depth after being transmitted in tissues are limited. Therefore, the FMT can merely reconstruct a tumor in a shallow surface, which severely restricts the application of the FMT in clinical practice.

Various reconstruction algorithms of FMT are capable of achieving high-sensitivity and high-resolution reconstruction effects for fluorescence sources distributed in a shallow layer. However, as the fluorescence sources move towards the depth, the intensity and distribution range of the fluorescence signals collected from the body surface are greatly weakened, which further worsens the reverse problem. Therefore, the fluorescence sources at the depth cannot be reconstructed by means of limited surface florescence signals. To overcome the shortcoming of the reconstruction algorithms, traditional technologies normally introduce a prior assumption of the spatial distribution of florescence sources in the reconstruction process, which may be divided into a guidance prior assumption and a non-guidance prior assumption. The non-guidance prior assumption designs the prior regularization based on the property of the fluorescence distribution. For example, a sparse prior regularization is capable of obtaining higher reconstructed signal-to-noise ratio and more accurate spatial position of the fluorescence sources. However, it still fails to solve the problem relating to the serious photon loss when the florescence sources are located at the depth. However, the traditional prior guidance normally adopts tomographic imaging with high structural resolution as a guidance mode, and the tumor area provided by this guidance mode is taken as the position and shape of the fluorescence source prior distribution to constrain the position and shape of the reconstruction result, for example, speculating the approximate position of the tumor based on the CT image. This method seriously depends on the imaging quality of the guidance mode. Moreover, the traditional guidance modes, such as CT, MRI and other structural imaging, do not specifically target tumors, have poor sensitivity, and fail to identify or segment small-sized tumors. Therefore, if the guidance mode fails to accurately provide prior structural information or there is misjudgment made by artificial segmentation, the quality of FMT reconstruction is severely reduced. It is necessary to introduce accurate prior information to achieve accurate directional guidance such that the shortcoming relating to the limited depth of FMT can be overcome.

In conclusion, the traditional prior guidance seriously depends on the imaging quality of the guidance mode. However, the traditional guidance mode has poor sensitivity and fail to identify or segment small-sized tumors, which severely reduces the quality of FMT reconstruction. Therefore, it is urgent to provide more accurate prior information to achieve accurate directional guidance such that the shortcoming relating to the limited depth of FMT can be overcome.

SUMMARY

To solve the technical problems in prior art, namely, technical problems relating to the lack of specificity of the guidance mode targeting the tumors, low accuracy and precision, failure of overcoming the limited depth of FMT, and the poor FMT reconstruction quality when the fluorescence source moves to the depth, the present invention provides a fluorescence molecular tomography reconstruction method based on prior guidance of magnetic particle imaging.

To achieve the above purpose, the present invention adopts the following technical solution:

The fluorescence molecular tomography reconstruction method based on prior guidance of magnetic particle imaging of the present invention, comprising:

Step 10: obtaining, by means of an optical/magnetic particle bimodal probe, an MPI (Magnetic Particle Imaging) three-dimensional tomographic image comprising tumor information in a detected living body, a body surface near-infrared fluorescence two-dimensional image, and a CT (Computed Tomography) image comprising anatomical structure information of tissues and organs around a tumor;

Step 20: taking the tumor as well as adjacent tissues and organs as a ROI (Region of Interest), constructing an SIS (Standard Imaging Space) capable of accommodating the ROI, and discretizing the SIS by using a finite element method;

Respectively performing threshold segmentation preprocessing on the CT image and the MPI three-dimensional tomographic image to obtain a preprocessed CT image and a preprocessed MPI three-dimensional tomographic image;

Step 30: encoding the discretized SIS to obtain a position vector $\vec{x}$; Mapping the body surface near-infrared fluorescence two-dimensional image to a discretized SIS surface to obtain a detected surface fluorescence signal $\vec{b}$;

Mapping the preprocessed CT image and the preprocessed MPI three-dimensional tomographic image into the interior of a discretized SIS, and respectively obtaining a prior $\vec{c}$ of the anatomical structure of tissues and organs around the tumor and a prior $\vec{m}$ of the tumor;

Step 40: performing forward model calculation based on SIS after the surface mapping and internal mapping to obtain a linear relationship A between the surface fluorescence signal $\vec{b}$ and the internal three-dimensional fluorescence distribution;

Step 50: establishing an objective function $E(\vec{x})$ of fluorescence molecular tomography reconstruction based on the linear relationship A and the position vector $\vec{x}$; constructing a Laplacian regularization matrix L for constraining the fluorescence molecular tomography reconstruction according to the prior $\vec{c}$ of the anatomical structure and the prior $\vec{m}$ of the tumor;

Step 60: based on the Laplacian regularization matrix L, selecting an iteration method for solving an objective function, and iteratively solving the objective function $E(\vec{x})$ to obtain a fluorescence molecular tomography reconstruction result $\vec{x}*$;

In another preferred embodiment of the present invention, the optical/magnetic particle bimodal probe is a probe that combines with a fluorescent dye, superparamagnetic iron oxide nanoparticles and a molecular target.

In another preferred embodiment of the present invention, in step 30, mapping the preprocessed CT image into the interior of a discretized SIS, comprising:

Taking the center coordinate of the discretized SIS as an imaging space center of the CT image;

Taking each pixel of the preprocessed CT image as a voxel point, obtaining the nearest grid node of the current voxel point in the discretized SIS, and giving the properties of the organ corresponding to the current voxel point to the grid node;

Going through the voxel points corresponding to each pixel, mapping the preprocessed CT image into the discretized SIS, and obtaining the prior $\vec{c}$ of the anatomical structure of the tissues and organs around the tumor;

In another preferred embodiment of the present invention, in step 30, mapping the preprocessed MPI three-dimensional tomographic image into the interior of a discretized SIS, comprising:

Arranging registration reference points, and adjusting the imaging spatial coordinate system of the MPI three-dimensional tomographic image to be consistent with the imaging spatial coordinate system of the CT image;

Performing a registration according to the mark points and adjusting the MPI spatial coordinate system to be consistent with the CT imaging space, thereby improving the accuracy and credibility of the registration;

Adjusting the resolution of the MPI three-dimensional tomographic image and the CT image to the same by adopting an interpolation method or super-resolution method;

Taking each pixel of the preprocessed MPI three-dimensional tomographic image as a voxel point, obtaining the nearest grid node of the current voxel point in the discretized SIS, and giving the magnetic particle concentration at the spatial position corresponding to the current voxel point to the grid node;

Going through the voxel points corresponding to each pixel, mapping the preprocessed MPI three-dimensional tomographic image into the discretized SIS, and obtaining the prior $\vec{m}$ of the tumor.

In another preferred embodiment of the present invention, the objective function $E(\vec{x})$ of fluorescence molecular tomography reconstruction is expressed as equation:

$$E(\vec{x}) = \frac{1}{2}\|A\vec{x} - \vec{b}\|_2^2 + \lambda \|L\vec{x}\|_p^p$$

wherein $\lambda$ represents the regularization parameter, L represents the Laplace regularization matrix, $\|\cdot\|_2^2$ represents the square of the vector 2 norm, and $\|\cdot\|_p^p$ represents the P-power of the vector P norm.

In another preferred embodiment of the present invention, the regularization parameter $\lambda$ is obtained through manual debugging and optimization or automatic optimization of curve L.

In another preferred embodiment of the present invention, P norm is an L1 norm or L2 norm selected according to the type of the reconstruction object.

In another preferred embodiment of the present invention, in step 50, constructing a Laplacian regularization matrix L for constraining the fluorescence molecular tomography reconstruction according to the prior $\vec{c}$ of the anatomical structure and the prior $\vec{m}$ of the tumor, comprising:

Merging the subspaces corresponding to different organs or tissues in the preprocessed CT image and the subspaces corresponding to the positions and shapes of tumors and different organs or tissues in the preprocessed MPI three-dimensional tomographic image to obtain a merged space S;

Constructing the Laplace regularization matrix L based on the merged space S, $$L = (l_{i,j})_{N \times N}$$

$$l_{i,j} = \begin{cases} 1 & i = j \\ -\rho_{S_k} e^{\left(\frac{-d_{i,j}^2}{4R^2}\right)} & i, j \in S_k \ \& \ i \neq j \\ 0 & \text{others} \end{cases}$$

$$\rho_{S_k} = 1 / \left( \sum_{\forall g, h \in S_k, g \neq h} e^{\left(\frac{-d_{g,h}^2}{4R^2}\right)} \right)$$

wherein $l_{i,j}$ represents the elements in row i and column j of the Laplace matrix, R represents the Gaussian kernel radius, $d_{i,j}$ represents the Euclidean distance between the grid node i and the grid node j in the merged space S, $d_{g,h}$ represents the Euclidean distance between the grid node g and the grid node h in the subspace $S_k$, $S_k$ represents the subspace k in the merged space, N×N represents the dimension of the Laplace matrix, and N represents the number of all discretized points in SIS space.

In another aspect of the present invention, a fluorescence molecular tomography reconstruction system based on prior guidance of magnetic particle imaging, comprising:

An image collection module used for obtaining an MPI (Magnetic Particle Imaging) three-dimensional tomographic image comprising tumor information in a detected living body, a body surface near-infrared fluorescence two-dimensional image, and a CT (Computed Tomography) image comprising anatomical structure information of tissues and organs around a tumor by means of an optical/magnetic particle bimodal probe, An SIS construction and discretization module used for taking the tumor as well as adjacent tissues and organs as a ROI (Region of Interest), constructing an SIS capable of accommodating the ROI, and discretizing the SIS by using a finite element method, An image preprocessing module used for performing threshold segmentation preprocessing on the CT image and the MPI three-dimensional tomographic image to obtain a preprocessed CT image and a preprocessed MPI three-dimensional tomographic image, An encoding mapping module used for encoding the discretized SIS to obtain a position vector $\vec{x}$, mapping the body surface near-infrared fluorescence two-dimensional image to a discretized SIS surface to obtain a detected surface fluorescence signal $\vec{b}$, mapping the preprocessed CT image and the preprocessed MPI three-dimensional tomographic image into the interior of a discretized SIS, and respectively obtaining a prior $\vec{c}$ of the anatomical structure of tissues and organs around the tumor and a prior $\vec{m}$ of the tumor, A forward model calculation module used for performing forward model calculation based on the SIS after the surface mapping and internal mapping to obtain a linear relationship A between the surface fluorescence signal $\vec{b}$ and the internal three-dimensional fluorescence distribution, An objective function construction model used for establishing an objective function $E(\vec{x})$ of fluorescence molecular tomography reconstruction based on the linear relationship between the surface fluorescence signal $\vec{b}$ and the internal three-dimensional fluorescence distribution, A regularization constraining construction module used for constructing a Laplacian regularization matrix L for constraining the fluorescence molecular tomography reconstruction according to the prior $\vec{c}$ of the anatomical structure and the prior $\vec{m}$ of the tumor, and A fluorescence molecular tomography reconstruction module used for selecting an iteration method for solving an objective function based on the Laplacian regularization matrix L, and iteratively solving the objective function $E(\vec{x})$ to obtain a fluorescence molecular tomography reconstruction result $\vec{x}^*$.

In another aspect of the present invention, an electronic device comprises at least one processor and a memory connected to at least one processor, wherein the memory stores instructions that can be executed by the processor, and the instructions are executed by the processor to realize the fluorescence molecular tomography reconstruction method based on prior guidance of magnetic particle imaging.

Compared with the prior art, the present invention has the following advantages:

The present invention uses MPI as a prior guidance for the FMT reconstruction according to the fluorescence molecular tomography reconstruction method based on prior guidance of magnetic particle imaging; compared with traditional CT, MRI and other guided modes, MPI is capable of specifically targeting tumor tissues based on a magnetic particle tracer, has high sensitivity, does not need a manual determination of tumor areas, able to provide accurate tumor prior information, thus overcoming the shortcoming of the limited depth of FMT while effectively improving the FMT reconstruction quality when the fluorescence source moves to the depth;

According to the fluorescence molecular tomography reconstruction method based on prior guidance of magnetic particle imaging and combined with the prior information of anatomical structure of surrounding tissues and organs provided by the CT image, the present invention designs a Laplace regularization matrix based on Gaussian weight, which is capable of giving different variance penalties according to the distance difference between grid nodes, thereby ensure the similarity of light intensity among close grid point pairs and the difference of light intensity among remote grid point pairs; thus, the reconstruction result is effectively prevented from being too smooth.

BRIEF DESCRIPTION OF THE DRAWINGS

By referring to the drawings and the detailed description of the embodiments, other features, purposes and advantages of the present invention become clearer.

DETAILED DESCRIPTION

Figure 1:
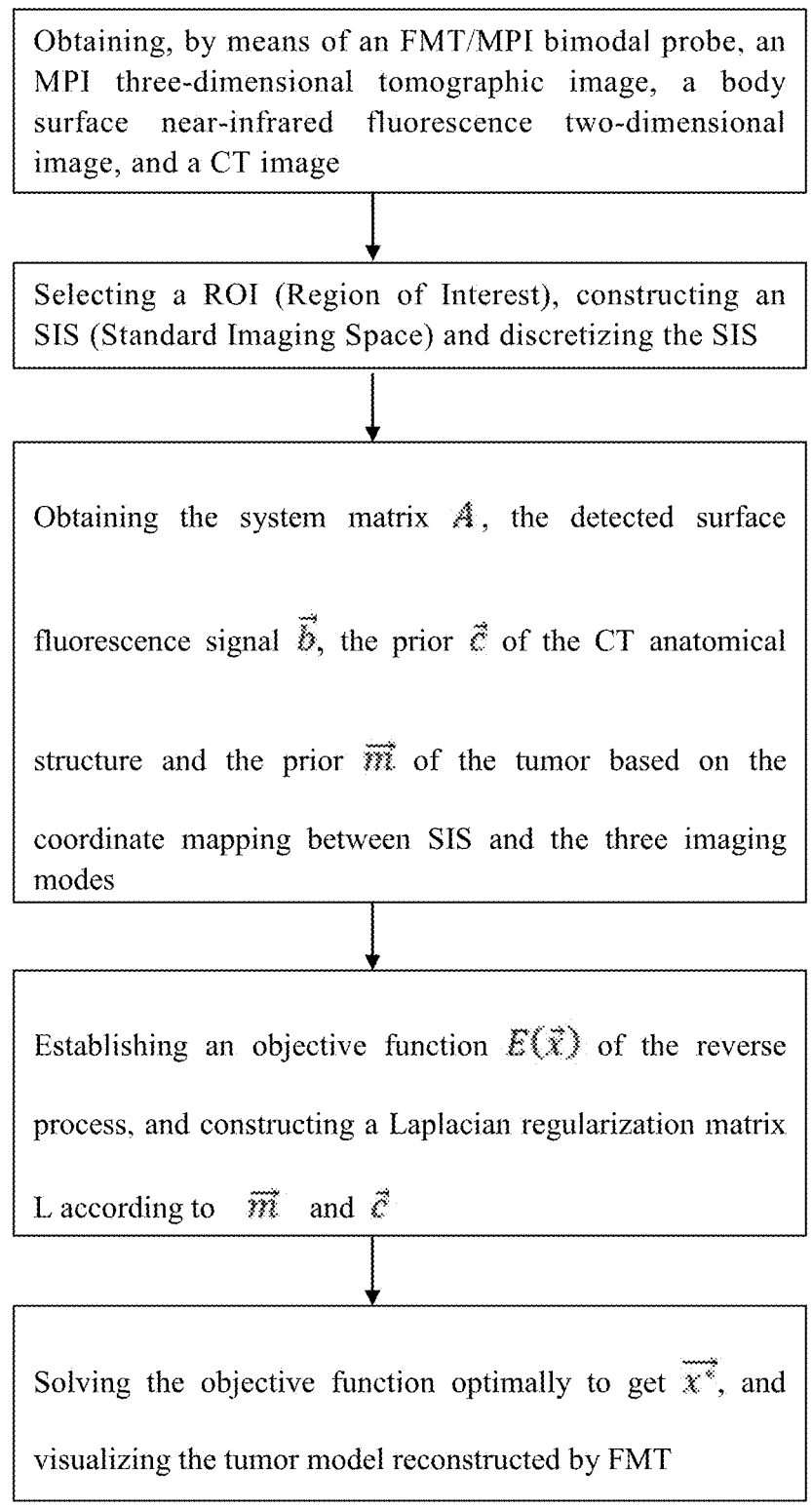
FIG. 1 is a schematic diagram illustrating a flowchart of the fluorescence molecular tomography reconstruction method based on prior guidance of magnetic particle imaging of the present invention.

The specific embodiments of the invention have been described in detail. The particular arrangements disclosed are meant to be illustrative only and not limiting as to the scope of the invention which is to be given the full breadth of the claims appended and any and all equivalents thereof. It should be noted that, for the convenience of description, only the parts relevant to the present invention are shown in the drawings.

It is worth mentioning that the embodiments and the features in the embodiments of the invention may be combined when there is no conflict. Detailed embodiments and drawings are combined hereinafter to elaborate the present invention.

The present invention provides a fluorescence molecular tomography reconstruction method based on prior guidance of magnetic particle imaging. According to the method of the present invention, MPI (Magnetic Particle Imaging) is used as prior information to provide more accurate directional guidance to overcome the shortcoming of the limited depth of FMT (Fluorescence molecular Imaging). Magnetic particle imaging reconstructs the particle concentration distribution at various locations in space through the nonlinear magnetization response of superparamagnetic nanoparticles. Because MPI information is based on the electromagnetic wave propagated after the particles are magnetized in a high-frequency alternating excitation field detected by the receiving coil, the energy loss of electromagnetic wave does not occur nearly in a short measuring distance. Therefore, its imaging accuracy is not limited by depth. In addition, compared with traditional guidance modes such as CT and MRI, MPI, as a functional imaging, is capable of displaying the distribution of magnetic particle probes in tumor tissues with high sensitivity and specificity, and meanwhile, it does not require manual participation. Therefore, MPI is more suitable for being used as a guidance mode for solving the problem relating to the limited depth of FMT reconstruction.

Figure 2:
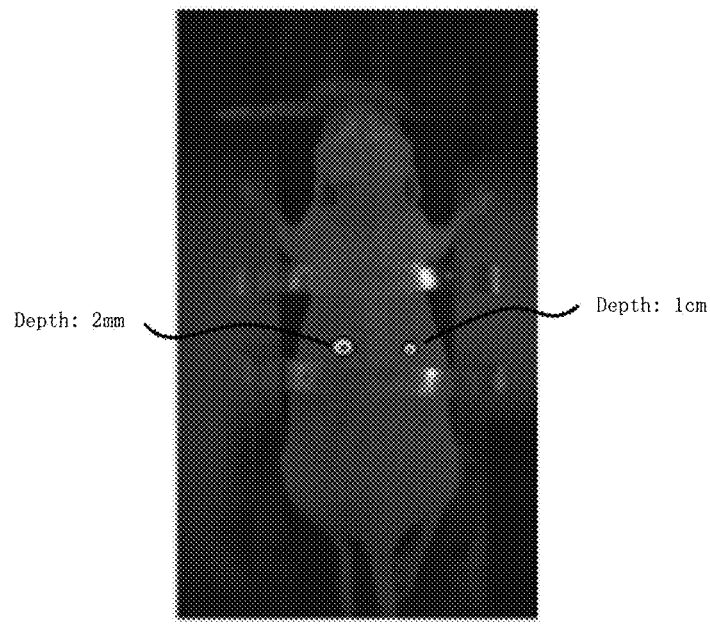
FIG. 2 is a schematic diagram illustrating the imaging result of near-infrared fluorescence imaging for tumors at different depths in the prior art.

FIG. 2 shows the imaging result of near-infrared fluorescence imaging for tumors at different depths in the prior art. It can be seen from FIG. 2 that near-infrared fluorescence imaging achieves a better reconstruction effect on the shallow surface. However, when comparing the reconstruction results at the depths of 2 mm and 1 mm, it can be clearly seen that, along the deepening of depth, the number of fluorescence photons generated by the fluorescent light source that can reach the surface after being transmitted in tissues is limited, and the reconstruction result is poorer than that on the shallow surface.

The fluorescence molecular tomography reconstruction method based on prior guidance of magnetic particle imaging of the present invention, comprising:

Step 10: obtaining, by means of an optical/magnetic particle bimodal probe, an MPI (Magnetic Particle Imaging) three-dimensional tomographic image comprising tumor information in a detected living body, a body surface near-infrared fluorescence two-dimensional image, and a CT (Computed Tomography) image comprising anatomical structure information of tissues and organs around a tumor;

Step 20: taking the tumor as well as adjacent tissues and organs as a ROI (Region of Interest), constructing an SIS (Standard Imaging Space) capable of accommodating the ROI, and discretizing the SIS by using a finite element method;

Respectively performing threshold segmentation preprocessing on the CT image and the MPI three-dimensional tomographic image to obtain a preprocessed CT image and a preprocessed MPI three-dimensional tomographic image;

Step 30: encoding the discretized SIS to obtain a position vector $\vec{x}$;

Mapping the body surface near-infrared fluorescence two-dimensional image to a discretized SIS surface to obtain a detected surface fluorescence signal $\vec{b}$;

Mapping the preprocessed CT image and the preprocessed MPI three-dimensional tomographic image into the interior of a discretized SIS, and respectively obtaining a prior $\vec{c}$ of the anatomical structure of tissues and organs around the tumor and a prior $\vec{m}$ of the tumor;

Step 40: performing forward model calculation based on SIS after the surface mapping and internal mapping to obtain a linear relationship A between the surface fluorescence signal $\vec{b}$ and the internal three-dimensional fluorescence distribution;

Step 50: establishing an objective function $E(\vec{x})$ of fluorescence molecular tomography reconstruction based on the linear relationship A and the position vector $\vec{x}$; constructing a Laplacian regularization matrix L for constraining the fluorescence molecular tomography reconstruction according to the prior $\vec{c}$ of the anatomical structure and the prior $\vec{m}$ of the tumor;

Step 60: based on the Laplacian regularization matrix L, selecting an iteration method for solving an objective function, and iteratively solving the objective function $E(\vec{x})$ to obtain a fluorescence molecular tomography reconstruction result $\vec{x}^*$;

To clearly illustrate the fluorescence molecular tomography reconstruction method based on prior guidance of magnetic particle imaging of the present invention, the steps in embodiments of the present invention are described in detail below in combination with FIG. 1.

Figure 3:
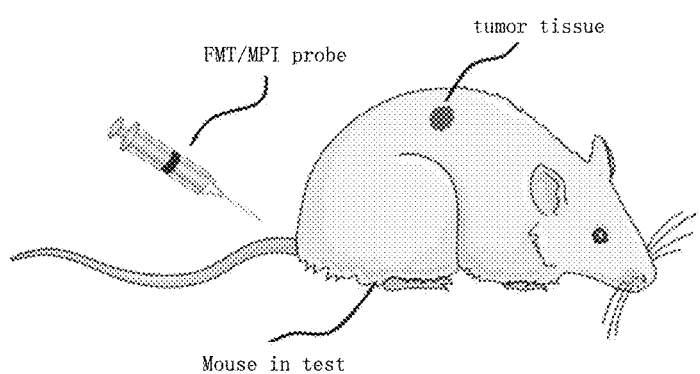
FIG. 3 is a schematic diagram illustrating an FMT/MPI bimodal probe fed into a mouse model of tumor of the fluorescence molecular tomography reconstruction method based on prior guidance of magnetic particle imaging in an embodiment of the present invention.

The fluorescence molecular tomography reconstruction method based on prior guidance of magnetic particle imaging in embodiment 1 of the present invention, comprising steps 10-60:

Step 10: obtaining, by means of an optical/magnetic particle bimodal probe, an MPI (Magnetic Particle Imaging) three-dimensional tomographic image comprising tumor information in a detected living body, a body surface near-infrared fluorescence two-dimensional image, and a CT (Computed Tomography) image comprising anatomical structure information of tissues and organs around the tumor;

The optical/magnetic particle bimodal probe is a probe that combines with a fluorescent dye, superparamagnetic iron oxide nanoparticles and a molecular target; the specificity of the probe targeting the tumors is combined to obtain two functional images of the same detected living body through two imaging modes;

FIG. 3 is a schematic diagram illustrating an FMT/MPI bimodal probe fed into a mouse model of tumor of the fluorescence molecular tomography reconstruction method based on prior guidance of magnetic particle imaging in an embodiment of the present invention, wherein the optical probe is used for an FMT imaging mode, which may be ICG or IRDye800CW, etc.; the magnetic particle probe is used for an MPI imaging mode, usually adopting iron oxide nanoparticles such as Perimag, VivoTrax and Synomag, etc.

Figure 4:
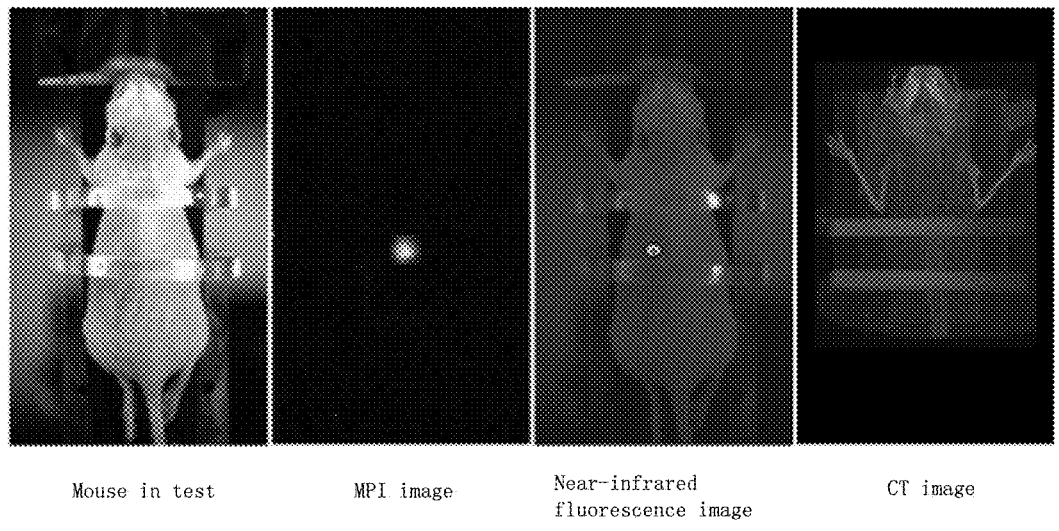
FIG. 4 is a schematic diagram illustrating an example of the imaging results of three imaging modes including MPI, near-infrared fluorescence and CT of the fluorescence molecular tomography reconstruction method based on prior guidance of magnetic particle imaging in an embodiment of the present invention.

FIG. 4 is a schematic diagram illustrating an example of the imaging results of three imaging modes including MPI, near-infrared fluorescence and CT of the fluorescence molecular tomography reconstruction method based on prior guidance of magnetic particle imaging in an embodiment of the present invention; first, the anatomical structure information (namely, the CT image in FIG. 4) of the detected living body is captured by using an X-ray emission and acquisition device; after the FMT/MPI bimodal probe is fed for a period of time, a fluorescence molecular tomography device is used to capture a fluorescent light spot on the surface of a detected living body to obtain a near-infrared fluorescence two-dimensional image (namely, a near-infrared fluorescence image in FIG. 4), and a magnetic particle imaging device is used to obtain an MPI three-dimensional tomographic image (namely, the MPI image in FIG. 4) of the magnetic particle magnetization response of the tumor site;

Step 20: taking the tumor as well as adjacent tissues and organs as a ROI (Region of Interest), constructing an SIS capable of accommodating the ROI, and discretizing the SIS by using a finite element method;

A ROI (Region of Interest) contains a tumor and its surrounding tissues or organs; for example, if the tested object is a mouse, the size of the SIS is set to 20×20×10 mm$^3$, and the SIS is discretized into spatial volume grids by using a grid-partition tool;

In an embodiment of the present invention, the SIS is discretized by using a finite element method; the grid cell may be a hexahedron grid cell or a wedge grid cell; the density of the grid cells, namely, the number of nodes and number of grid cells, may be appropriately adjusted according to the requirements of the model.

Figure 5:
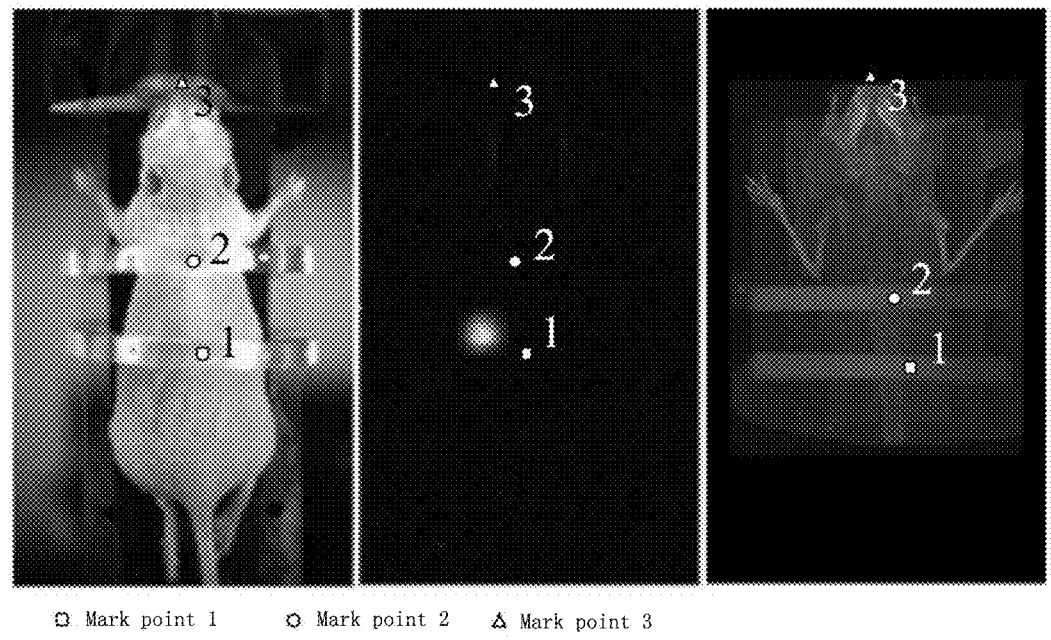
FIG. 5 is a schematic diagram illustrating registration reference points arranged when performing a spatial registration of the MPI and CT imaging spaces of the fluorescence molecular tomography reconstruction method based on prior guidance of magnetic particle imaging in an embodiment of the present invention.

Respectively performing threshold segmentation preprocessing on the CT image and the MPI three-dimensional tomographic image to obtain a preprocessed CT image and a preprocessed MPI three-dimensional tomographic image;

Step 30: encoding the discretized SIS to obtain a position vector $\vec{x}$;

Mapping the body surface near-infrared fluorescence two-dimensional image to a discretized SIS surface to obtain a detected surface fluorescence signal $\vec{b}$;

Mapping the preprocessed CT image and the preprocessed MPI three-dimensional tomographic image into the interior of a discretized SIS, and respectively obtaining a prior $\vec{c}$ of the anatomical structure of tissues and organs around the tumor and a prior $\vec{m}$ of the tumor;

Mapping the preprocessed CT image into the interior of a discretized SIS, comprising:

Taking the center coordinate of the discretized SIS as an imaging space center of the CT image;

At this point, the SIS merely includes spatial volume grids and does not contain any anatomical parts; the center of the SIS is taken as the imaging center of the CT image; namely, a fixed reference point of an anatomical part is determined for the SIS according to the CT imaging space, and then other anatomical parts are determined and mapped according to the anatomical structural relationship;

Taking each pixel of the preprocessed CT image as a voxel point, obtaining the nearest grid node of the current voxel point in the discretized SIS, and giving the properties of the organ corresponding to the current voxel point to the grid node;

The properties of the organ include the fluorescence scattering coefficient and absorption coefficient, etc.;

Going through the voxel points corresponding to each pixel, mapping the preprocessed CT image into the discretized SIS, and obtaining the prior $\vec{c}$ of the anatomical structure of the tissues and organs around the tumor;

Mapping the preprocessed MPI three-dimensional tomographic image into the interior of a discretized SIS, comprising:

Arranging registration reference points, and adjusting the imaging spatial coordinate system of the MPI three-dimensional tomographic image to be consistent with the imaging spatial coordinate system of the CT image;

For the same object in the imaging field of CT and MPI modes, markers are arranged on a fixed device for the detected object as registration reference points; for example, containers containing a small number of bimodal probes are respectively placed on bandages on the mouse, as well as the head and tail portions of the mouse's bed as markers; FIG. 5 shows registration reference points arranged when performing a spatial registration of the MPI and CT imaging spaces of the fluorescence molecular tomography reconstruction method based on prior guidance of magnetic particle imaging in an embodiment of the present invention, wherein mark point 1 and mark point 2 are respectively arranged on the two bandages on the mouse, and mark point 3 is arranged on the head portion of the mouse's bed;

Performing a registration according to the mark points and adjusting the MPI spatial coordinate system to be consistent with the CT imaging space, thereby improving the accuracy and credibility of the registration;

Adjusting the resolution of the MPI three-dimensional tomographic image and the CT image to the same by adopting an interpolation method or super-resolution method;

There are great differences in the resolution between the MPI imaging mode and the CT imaging mode; for example, the resolution of CT reaches 0.146 mm, while the resolution of the most advanced MPI imaging equipment merely reaches about 1 mm; if the resolution of the MPI image is not consistent with the CT image, an precise coordinate mapping cannot be achieved; traditional interpolation methods such as a cubic spline interpolation method and a bicubic interpolation method may be adopted to improve the spatial resolution of MPI, but the resolution difference between the two modes reaches R(MPI):R(CT)=5.29; when the precision of a simple interpolation method is insufficient, the relatively mature and commonly-used hyper-resolution network models based on deep learning, such as SRGAN and ESRGAN, may be adopted to improve the resolution of MPI;

Taking each pixel of the preprocessed MPI three-dimensional tomographic image as a voxel point, obtaining the nearest grid node of the current voxel point in the discretized SIS, and giving the magnetic particle concentration at the spatial position corresponding to the current voxel point to the grid node;

Going through the voxel points corresponding to each pixel, mapping the preprocessed MPI three-dimensional tomographic image into the discretized SIS, and obtaining the prior $\vec{m}$ of the tumor;

Based on a standard imaging space, assuming that the fluorescence source is excited and the fluorescent light on the body surface is collected from four directions, describing the transmission process of the fluorescence photon in the tissues of the imaging object by the coupling diffusion approximation equations shown in equations (1) and (2), and describing the refractive index deviation between the object surface and the air by the Robin boundary conditions shown in equation (3):

$$-\nabla D_x(r)\nabla \Phi_x(r) + \mu_{ax}(r)\Phi_x(r) = \Theta\delta(r - r_l), r \in \Omega \quad (1)$$

$$-\nabla D_m(r)\nabla \Phi_m(r) + \mu_{am}(r)\Phi_m(r) = \Phi_x(r)\eta\mu_{af}(r), r \in \Omega \quad (2)$$

$$2D_{x,m}(r)\frac{\partial \Phi_{x,m}(r)}{\partial \vec{n}(r)} + q\Phi_{x,m}(r) = 0, r \in \Omega \quad (3)$$

wherein $D_x$ represents the diffusion coefficient of the fluorescence photon excitation process, $D_m$ represents the diffusion coefficient of the fluorescence photon emission process, $\mu_{ax}$ represents the optical absorption coefficient, $\mu_{am}$ represents the optical scattering coefficient, $\Phi_x$ represents the optical density of the fluorescence photon excitation process, $\Phi_m$ represents the optical density of the fluorescence photon emission process, $\Theta\delta(r-r_l)$ represents the point excitation fluorescence source, $r_l$ represents the position of the fluorescence source, $\delta$ represents the Dirac function, $\Theta$ represents the intensity of the point excitation fluorescence source, $\Omega$ represents the imaging space, $\eta\mu_{af}(r)$ represents the three-dimensional spatial distribution of the fluorescence source in organic tissues, $\delta\Omega$ represents the edge of the imaging object, $\vec{n}$ represents the outward unit normal vector on the edge, and q represents the deviation of the optical refractive index between the boundary of the imaging object and the air;

Obtaining the linear relationship between the surface fluorescence signal $\vec{b}$ and the internal three-dimensional fluorescence distribution A by using the finite element discrete solution of the above equation, namely, the system matrix A; at this point, the forward process of the photon transmission from the tumor fluorescence source to body surface is expressed as equation (4):

$$A\vec{x} = \vec{b} \tag{4}$$

Step 50: establishing an objective function $E(\vec{x})$ of fluorescence molecular tomography reconstruction based on the linear relationship A and the position vector $\vec{x}$; constructing a Laplacian regularization matrix L for constraining the fluorescence molecular tomography reconstruction according to the prior $\vec{c}$ of the anatomical structure and the prior $\vec{m}$ of the tumor;

The objective function $E(\vec{x})$ of fluorescence molecular tomography reconstruction is expressed as equation (5):

$$E(\vec{x}) = \frac{1}{2}\|A\vec{x} - \vec{b}\|_2^2 + \lambda\|L\vec{x}\|_p^p \tag{5}$$

wherein $\lambda$ represents the regularization parameter, L represents the Laplace regularization matrix, $\|\cdot\|_2^2$ represents the square of the vector 2 norm, and $\|\cdot\|_p^p$ represents the P-power of the vector P norm;

The regularization parameter $\lambda$ is obtained through manual debugging and optimization or automatic optimization of curve L;

P norm is an L1 norm or L2 norm selected according to the type of the reconstruction object; when the reconstruction object is a sparse fluorescence source, L1 norm is selected as the regularization, and when the structural integrity of the reconstruction object needs to be ensured, L2 norm is selected as the regularization;

Constructing a Laplacian regularization matrix L for constraining the fluorescence molecular tomography reconstruction according to the prior $\vec{c}$ of the anatomical structure and the prior $\vec{m}$ of the tumor, comprising:

Merging the subspaces $\{S_{liver}, S_{heart}, \ldots, S_{lung}\}$ corresponding to different organs or tissues ($S_{liver}$ represents the subspace of the liver, $S_{heart}$ represents the subspace of the heart and $S_{lung}$ represents the subspace of the lung in the thoracic cavity) in the preprocessed CT image and the subspaces $S_{tumor}$ (the anatomical structure vector $\vec{c}$ provides the positions and shapes of different tissues or organs in the region of interest, and the tumor prior vector provides the positions and shapes of the tumors) corresponding to the positions and shapes of tumors and different organs or tissues in the preprocessed MPI three-dimensional tomographic image to obtain a merged space $S = \{S_1, S_2, \ldots, S_k, \ldots S_K\}$, (k=1, 2, ..., K), wherein the numeric index corresponds to a certain organ or tissue, such as $S_1 \to S_{liver}$;

Constructing the Laplace regularization matrix L based on the merged space S, as shown in equations (6)-(8):

$$L = (l_{i,j})_{N \times N} \tag{6}$$

$$l_{i,j} = \begin{cases} 1 & i = j \\ -\rho_{S_k} e^{\left(\frac{-d_{i,j}^2}{4R^2}\right)} & i, j \in S_k \ \& \ i \neq j \\ 0 & \text{others} \end{cases} \tag{7}$$

$$\rho_{S_k} = 1 / \left( \sum_{\forall g,h \in S_k, g \neq h} e^{\left(\frac{-d_{g,h}^2}{4R^2}\right)} \right) \tag{8}$$

wherein $l_{i,j}$ represents the elements in row i and column j of the Laplace matrix, R represents the Gaussian kernel radius, $d_{i,j}$ represents the Euclidean distance between the grid node i and the grid node j in the merged space S, i,j represents the global index variable of the merged space S, $d_{g,h}$ represents the Euclidean distance between the grid node g and the grid node h in the subspace $S_k$, g,h represents the local index variable of the subspace $S_k$, $S_k$ represents the subspace k in the merged space, N×N represents the dimension of the Laplace matrix, and N represents the number of all discretized points in SIS space, wherein the Gaussian kernel radius R is used to adjust the convergence level; for example, in the reconstruction of the coefficient of multiple fluorescence sources, R=0.1 may be defined to enhance the sparse reconstruction ability;

Step 60: based on the Laplacian regularization matrix L, selecting an iteration method for solving an objective function, and iteratively solving the objective function $E(\vec{x})$ to obtain a fluorescence molecular tomography reconstruction result $\vec{x}^*$;

The alternating direction method of multipliers (ADMM) may be selected as the iterative method for solving the objective function.

Figure 6:
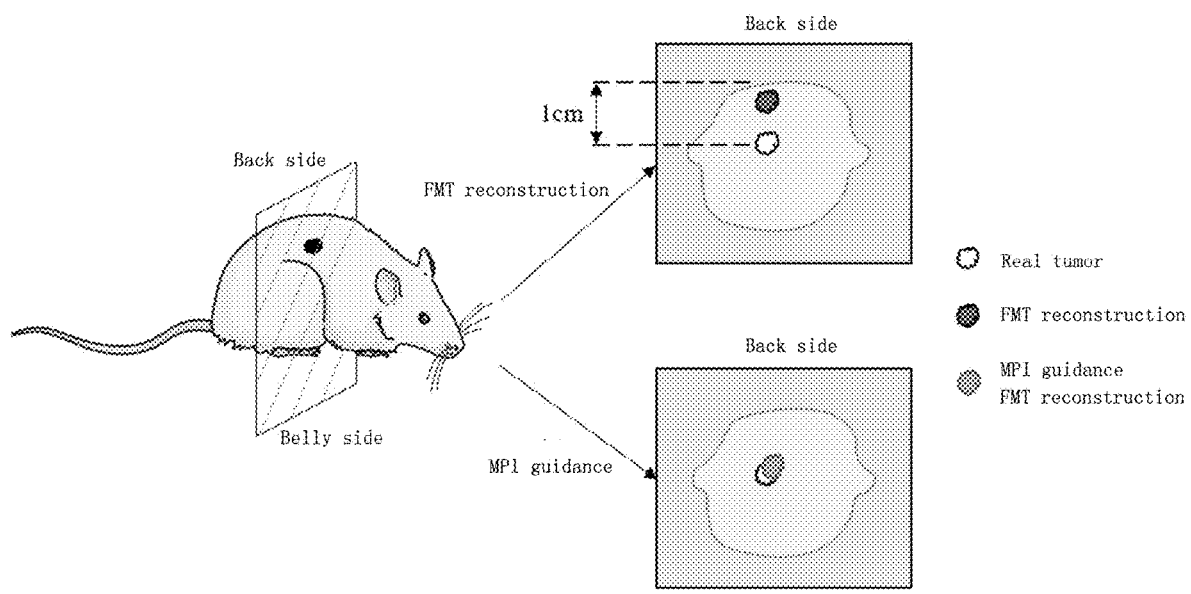
FIG. 6 is a schematic diagram illustrating the comparison between the traditional FMT reconstruction result and the MPI-guided FMT reconstruction result of the fluorescence molecular tomography reconstruction method based on prior guidance of magnetic particle imaging in an embodiment of the present invention.

FIG. 6 is a schematic diagram illustrating the comparison between the traditional FMT reconstruction result and the MPI-guided FMT reconstruction result of the fluorescence molecular tomography reconstruction method based on prior guidance of magnetic particle imaging in an embodiment of the present invention. It can be seen that the position of the reconstructed tumor in the traditional FMT reconstruction result is 1 cm (centimeter) different from that of the real position of the tumor, while the position of the reconstructed tumor in the MPI-guided FMT reconstruction result of the present invention is almost coincident with that of the real position of the tumor. It proves that the present invention effectively improves the accuracy of the reconstruction result, and the reconstruction result shows complete morphology and structure, clear tissue edges, and high accuracy of spatial position.

Although the steps in the embodiment are described in the aforesaid sequence, those skilled in the art shall understand that, to achieve the effect of this embodiment, steps may be performed in a different sequence. The steps may be performed simultaneously (in parallel) or in a reverse sequence. These simple variations shall all fall into the scope of the present invention.

In embodiment 2 of the present invention, a fluorescence molecular tomography reconstruction system based on prior guidance of magnetic particle imaging, comprising:

An image collection module used for obtaining an MPI (Magnetic Particle Imaging) three-dimensional tomographic image comprising tumor information in a detected living body, a body surface near-infrared fluorescence two-dimensional image, and a CT (Computed Tomography) image comprising anatomical structure information of tissues and organs around a tumor by means of an optical/magnetic particle bimodal probe;

An SIS construction and discretization module used for taking the tumor as well as adjacent tissues and organs as a ROI (Region of Interest), constructing an SIS capable of accommodating the ROI, and discretizing the SIS by using a finite element method;

An image preprocessing module used for performing threshold segmentation preprocessing on the CT image and the MPI three-dimensional tomographic image to obtain a preprocessed CT image and a preprocessed MPI three-dimensional tomographic image;

An encoding mapping module used for encoding the discretized SIS to obtain a position vector $\vec{x}$, mapping the body surface near-infrared fluorescence two-dimensional image to a discretized SIS surface to obtain a detected surface fluorescence signal $\vec{b}$, mapping the preprocessed CT image and the preprocessed MPI three-dimensional tomographic image into the interior of a discretized SIS, and respectively obtaining a prior $\vec{c}$ of the anatomical structure of tissues and organs around the tumor and a prior $\vec{m}$ of the tumor;

A forward model calculation module used for performing forward model calculation based on the SIS after the surface mapping and internal mapping to obtain a linear relationship A between the surface fluorescence signal $\vec{b}$ and the internal three-dimensional fluorescence distribution;

An objective function construction model used for establishing an objective function $E(\vec{x})$ of fluorescence molecular tomography reconstruction based on the linear relationship between the surface fluorescence signal $\vec{b}$ and the internal three-dimensional fluorescence distribution;

A regularization constraining construction module used for constructing a Laplacian regularization matrix L for constraining the fluorescence molecular tomography reconstruction according to the prior $\vec{c}$ of the anatomical structure and the prior $\vec{m}$ of the tumor;

A fluorescence molecular tomography reconstruction module used for selecting an iteration method for solving an objective function based on the Laplacian regularization matrix L, and iteratively solving the objective function $E(\vec{x})$ to obtain a fluorescence molecular tomography reconstruction result $\vec{x}^*$;

Those skilled in the art should clearly understand that, for the convenience and brevity of description, the specific operation and related description of the aforesaid system may refer to the corresponding process in the method of the present invention, and they are therefore briefly described herein.

It is worth mentioning that a fluorescence molecular tomography reconstruction system based on prior guidance of magnetic particle imaging in the embodiment of the present invention is merely illustrated by using the aforesaid functional modules. In practice, the aforesaid functions may be realized by different functional modules according to actual needs. Namely, the modules or steps in the embodiment of the present invention may be re-separated or combined. For example, the modules in the aforesaid embodiment may be combined into one module or further separated into a plurality of submodules to achieve all or a part of the functions described above. The names of the modules and steps involved in the embodiment of the present invention are merely used to distinguish each module or step but not intended to limit the present invention.

In embodiment 3 of the present invention, an electronic device of the present invention comprises at least one processor and a memory connected to at least one processor, wherein the memory stores instructions that can be executed by the processor, and the instructions are executed by the processor to realize the fluorescence molecular tomography reconstruction method based on prior guidance of magnetic particle imaging of the present invention.

In embodiment 4 of the present invention, a computer-readable storage medium is used to store computer instructions for being executed by a computer to realize the fluorescence molecular tomography reconstruction method based on prior guidance of magnetic particle imaging of the present invention.

Those skilled in the art should clearly understand that, for the convenience and brevity of description, the specific operation and related description of the aforesaid storage device and processing device may refer to the corresponding process in the method of the present invention, and they are therefore briefly described herein.

Those skilled in the art should realize that the modules, methods and steps described in each embodiment may be realized by an electronic hardware, computer software or a combination of both. The corresponding programs of software modules and steps may be installed in a random memory (RAM), read-only memory (ROM), electrically programmable ROM, electrically erasable programmable ROM, temporary storage, hard disk, removable disk, CD-ROM, or any other form of storage media known in the art. To clearly explain the interchangeability of electronic hardware and software, the steps in each embodiment have been described in general terms according to the functions in the above description. Whether these functions are implemented in electronic hardware or software depends on the specific application and design of the technical solution. Those skilled in the art may adopt different methods to achieve the described functions for each specific application, but these implementations should not be considered beyond the scope of the present invention.

The terms "first" and "second" are used to distinguish similar objects instead of describing or indicating a specific order or sequence.

The term "including" or any other similar term is intended to cover non-exclusive inclusion. Therefore, a process, method, article or equipment/device including a series of elements not only includes those elements, but also includes other elements not explicitly listed, or further includes elements inherent in these processes, methods, articles or equipment/devices.

The above are merely preferred embodiments of the present invention, and the scope of the present invention is not limited to the embodiments described above. All technical solutions obtained under the idea of the present invention shall fall into the scope of the present invention. It should be noted that equivalent modifications and replacements may be made by those skilled in the art without departing from the principles of the present invention. Therefore, these improvements and modifications shall also fall into the scope of the present invention.

What is claimed is:

1. A fluorescence molecular tomography reconstruction method based on prior guidance of magnetic particle imaging, comprising:
   obtaining, by means of an optical/magnetic particle bimodal probe, an Magnetic Particle Imaging (MPI) three-dimensional tomographic image comprising tumor information in a detected living body, a body surface near-infrared fluorescence two-dimensional image, and a Computed Tomography (CT) image comprising anatomical structure information of tissues and organs around a tumor;

taking the tumor, adjacent tissues and organs as a Region of interest (ROI), constructing an Standard Imaging Space (SIS) capable of accommodating the ROI, and discretizing the SIS using a finite element method;

respectively performing threshold segmentation preprocessing on the CT image and the MPI three-dimensional tomographic image to obtain a preprocessed CT image and a preprocessed MPI three-dimensional tomographic image;

encoding the discretized SIS to obtain a position vector $\vec{x}$;

mapping the body surface near-infrared fluorescence two-dimensional image to a discretized SIS surface to obtain a detected surface fluorescence signal $\vec{b}$;

taking the center coordinate of the discretized SIS as an imaging space center of the CT image, taking each pixel of the preprocessed CT image as a voxel point, obtaining the nearest grid node of the current voxel point in the discretized SIS, giving the properties of the organ corresponding to the current voxel point to the grid node, going through the voxel points corresponding to each pixel, mapping the preprocessed CT image into the discretized SIS, and obtaining the prior $\vec{c}$ of the anatomical structure of the tissues and organs around the tumor;

arranging registration reference points, adjusting the imaging spatial coordinate system of the MPI three-dimensional tomographic image to be consistent with the imaging spatial coordinate system of the CT image, performing a registration according to the mark points and adjusting the MPI spatial coordinate system to be consistent with the CT imaging space, thereby improving the accuracy and credibility of the registration, adjusting the resolution of the MPI three-dimensional tomographic image and the CT image to the same by adopting an interpolation method or super-resolution method, taking each pixel of the preprocessed MPI three-dimensional tomographic image as a voxel point, obtaining the nearest grid node of the current voxel point in the discretized SIS, giving the magnetic particle concentration at the spatial position corresponding to the current voxel point to the grid node, going through the voxel points corresponding to each pixel, and mapping the preprocessed MPI three-dimensional tomographic image into the discretized SIS, and obtaining the prior $\vec{m}$ of the tumor;

performing forward model calculation based on SIS after the surface mapping and internal mapping to obtain a linear relationship A between the surface fluorescence signal $\vec{b}$ and the internal three-dimensional fluorescence distribution;

establishing an objective function $E(\vec{x})$ of fluorescence molecular tomography reconstruction based on the linear relationship A and the position vector $\vec{x}$;

$$E(\vec{x}) = \frac{1}{2}\|A\vec{x} - \vec{b}\|_2^2 + \lambda\|L\vec{x}\|_p^p$$

wherein $\lambda$ represents the regularization parameter, L represents the Laplace regularization matrix, $\|\cdot\|_2^2$ represents the square of the vector 2 norm, and $\|\cdot\|_p^p$ represents the P-power of the vector P norm;

merging the subspaces corresponding to different organs or tissues in the preprocessed CT image and the subspaces corresponding to the positions and shapes of tumors and different organs or tissues in the preprocessed MPI three-dimensional tomographic image to obtain a merged space S;

constructing the Laplace regularization matrix L based on the merged space S, $$L = (l_{i,j})_{N \times N}$$

$$l_{i,j} = \begin{cases} 1 & i = j \\ -\rho_{S_k} e^{\left(\frac{-d_{i,j}^2}{4R^2}\right)} & i, j \in S_k \ \& \ i \neq j \\ 0 & \text{others} \end{cases}$$

$$\rho_{S_k} = 1 \Bigg/ \left( \sum_{\forall g, h \in S_k, g \neq h} e^{\left(\frac{-d_{g,h}^2}{4R^2}\right)} \right)$$

wherein $l_{i,j}$ represents the elements in row i and column j of the Laplace matrix, R represents the Gaussian kernel radius, $d_{i,j}$ represents the Euclidean distance between the grid node i and the grid node j in the merged space S, $d_{g,h}$ represents the Euclidean distance between the grid node g and the grid node h in the subspace $S_k$, $S_k$ represents the subspace k in the merged space, N×N represents the dimension of the Laplace matrix, and N represents the number of all discretized points in SIS space;

based on the Laplacian regularization matrix L, selecting an iteration method for solving an objective function, and iteratively solving the objective function $E(\vec{x})$ to obtain a fluorescence molecular tomography reconstruction result $\vec{x}^*$.

2. The fluorescence molecular tomography reconstruction method based on prior guidance of magnetic particle imaging of claim 1, wherein the optical/magnetic particle bimodal probe is a probe that combines with a fluorescent dye, superparamagnetic iron oxide nanoparticles and a molecular target.

3. The fluorescence molecular tomography reconstruction method based on prior guidance of magnetic particle imaging of claim 1, wherein the regularization parameter $\lambda$ is obtained through manual debugging and optimization or automatic optimization of curve L.

4. The fluorescence molecular tomography reconstruction method based on prior guidance of magnetic particle imaging of claim 1, wherein P norm is an L1 norm or L2 norm selected according to the type of the reconstruction object.

5. A fluorescence molecular tomography reconstruction system based on prior guidance of magnetic particle imaging, comprising:

an image collection module used for obtaining an MPI three-dimensional tomographic image comprising tumor information in a detected living body, a body surface near-infrared fluorescence two-dimensional image, and a CT image comprising anatomical structure information of tissues and organs around a tumor by means of an optical/magnetic particle bimodal probe, an SIS construction and discretization module used for taking the tumor as well as adjacent tissues and organs as a ROI, constructing an SIS capable of accommodating the ROI, and discretizing the SIS by using a finite element method, an image preprocessing module used for performing threshold segmentation preprocessing on the CT image and the MPI three-dimensional tomographic image to obtain a preprocessed CT image and a preprocessed MPI three-dimensional tomographic image, an encoding mapping module used for encoding the discretized SIS to obtain a position vector $\vec{x}$, mapping the body surface near-infrared fluorescence two-dimensional image to a discretized SIS surface to obtain a detected surface fluorescence signal $\vec{b}$, taking the center coordinate of the discretized SIS as an imaging space center of the CT image, taking each pixel of the preprocessed CT image as a voxel point, obtaining the nearest grid node of the current voxel point in the discretized SIS, giving the properties of the organ corresponding to the current voxel point to the grid node, going through the voxel points corresponding to each pixel, mapping the preprocessed CT image into the discretized SIS, obtaining the prior $\vec{c}$ of the anatomical structure of the tissues and organs around the tumor, arranging registration reference points, and adjusting the imaging spatial coordinate system of the MPI three-dimensional tomographic image to be consistent with the imaging spatial coordinate system of the CT image, performing a registration according to the mark points and adjusting the MPI spatial coordinate system to be consistent with the CT imaging space, thereby improving the accuracy and credibility of the registration, adjusting the resolution of the MPI three-dimensional tomographic image and the CT image to the same by adopting an interpolation method or super-resolution method, taking each pixel of the preprocessed MPI three-dimensional tomographic image as a voxel point, obtaining the nearest grid node of the current voxel point in the discretized SIS, giving the magnetic particle concentration at the spatial position corresponding to the current voxel point to the grid node, going through the voxel points corresponding to each pixel, mapping the preprocessed MPI three-dimensional tomographic image into the discretized SIS, and obtaining the prior $\vec{m}$ of the tumor, a forward model calculation module used for performing forward model calculation based on the SIS after the surface mapping and internal mapping to obtain a linear relationship A between the surface fluorescence signal $\vec{b}$ and the internal three-dimensional fluorescence distribution, an objective function construction model used for establishing an objective function $E(\vec{x})$ of fluorescence molecular tomography reconstruction based on the linear relationship between the surface fluorescence signal $\vec{b}$ and the internal three-dimensional fluorescence distribution, $$E(\vec{x}) = \frac{1}{2}\|A\vec{x} - \vec{b}\|_2^2 + \lambda \|L\vec{x}\|_p^p$$

wherein $\lambda$ represents the regularization parameter, L represents the Laplace regularization matrix, $\|\bullet\|_2^2$ represents the square of the vector 2 norm, and $\|\bullet\|_p^p$ represents the P-power of the vector P norm, merging the subspaces corresponding to different organs or tissues in the preprocessed CT image and the subspaces corresponding to the positions and shapes of tumors and different organs or tissues in the preprocessed MPI three-dimensional tomographic image to obtain a merged space S;

constructing the Laplace regularization matrix L based on the merged space S, $$L = (l_{i,j})_{N \times N}$$

$$L = (l_{i,j})_{N \times N}$$

$$l_{i,j} = \begin{cases} 1 & i = j \\ -\rho_{S_k} e^{\left(\frac{-d_{i,j}^2}{4R^2}\right)} & i, j \in S_k \, \& \, i \neq j \\ 0 & \text{others} \end{cases}$$

$$\rho_{S_k} = 1 / \left( \sum_{\forall g, h \in S_k, g \neq h} e^{\left(\frac{-d_{g,h}^2}{4R^2}\right)} \right)$$

wherein $l_{i,j}$ represents the elements in row i and column j of the Laplace matrix, R represents the Gaussian kernel radius, $d_{i,j}$ represents the Euclidean distance between the grid node i and the grid node j in the merged space S, $d_{g,h}$ represents the Euclidean distance between the grid node g and the grid node h in the subspace $S_k$, $S_k$ represents the subspace k in the merged space, N×N represents the dimension of the Laplace matrix, and N represents the number of all discretized points in SIS space; and A fluorescence molecular tomography reconstruction module used for selecting an iteration method for solving an objective function based on the Laplacian regularization matrix L, and iteratively solving the objective function $E(\vec{x})$ to obtain a fluorescence molecular tomography reconstruction result $\vec{x}^*$.

6. An electronic device, comprising:

at least one processor, and a memory connected to at least one processor, wherein the memory stores instructions that can be executed by a processor, and the instructions are executed by the processor to realize the fluorescence molecular tomography reconstruction method based on prior guidance of magnetic particle imaging of claim 1.

* * * * *